(12) United States Patent
Foster et al.

(10) Patent No.: US 9,453,787 B2
(45) Date of Patent: Sep. 27, 2016

(54) MEMS-BASED SINGLE PARTICLE SEPARATION SYSTEM

(71) Applicant: Owl biomedical, Inc., Goleta, CA (US)

(72) Inventors: John S Foster, Santa Barbara, CA (US); Nicholas C. Martinez, Santa Barbara, CA (US)

(73) Assignee: Owl biomedical, Inc., Goleta, CA (US)

( * ) Notice: Subject to any disclaimer, the term of this patent is extended or adjusted under 35 U.S.C. 154(b) by 226 days.

(21) Appl. No.: 14/275,974

(22) Filed: May 13, 2014

(65) Prior Publication Data

US 2015/0253223 A1    Sep. 10, 2015

Related U.S. Application Data

(60) Provisional application No. 61/948,493, filed on Mar. 5, 2014.

(51) Int. Cl.

| | | |
|---|---|---|
| G01N 33/00 | (2006.01) | |
| G01N 1/30 | (2006.01) | |
| G01N 1/31 | (2006.01) | |
| B01L 3/02 | (2006.01) | |
| B01L 3/00 | (2006.01) | |

(52) U.S. Cl.
CPC ............... *G01N 1/30* (2013.01); *B01L 3/0241* (2013.01); *B01L 3/502738* (2013.01); *B01L 3/502761* (2013.01); *G01N 1/31* (2013.01); *B01L 3/502715* (2013.01); *B01L 2200/0652* (2013.01); *B01L 2300/0663* (2013.01); *B01L 2300/0864* (2013.01); *B01L 2400/0622* (2013.01); *B01L 2400/0644* (2013.01)

(58) Field of Classification Search
CPC ..... G01N 1/30; G01N 1/31; B01L 3/502738
See application file for complete search history.

(56) References Cited

U.S. PATENT DOCUMENTS

| | | |
|---|---|---|
| 6,838,056 B2 | 1/2005 | Foster |
| 6,941,005 B2 | 9/2005 | Lary et al. |
| 7,214,298 B2 | 5/2007 | Spence et al. |
| 7,220,594 B2 | 5/2007 | Foster et al. |
| 7,229,838 B2 | 6/2007 | Foster et al. |
| 7,264,972 B2 | 9/2007 | Foster |
| 7,745,221 B2 | 6/2010 | Butler et al. |
| 2007/0178529 A1* | 8/2007 | Breidford ............... B01F 11/04 435/7.1 |
| 2008/0261295 A1 | 10/2008 | Butler et al. |
| 2011/0030808 A1 | 2/2011 | Chiou et al. |
| 2012/0255373 A1 | 10/2012 | Foster et al. |

OTHER PUBLICATIONS

U.S. Appl. No. 13/374,899, filed Jan. 23, 2012, Foster, et al.
U.S. Appl. No. 13/374,89, filed Jan. 23, 2012, Foster et al.

* cited by examiner

*Primary Examiner* — Sam P Siefke
(74) *Attorney, Agent, or Firm* — Jaquelin K. Spong

(57) ABSTRACT

A particle separation system uses a MEMS-based, microfabricated particle manipulation device which has an inlet channel, output channels, and a movable member formed on a substrate to sort one or more target particle from a sample stream. The system may include an interposer that receives the sorted particle and dispenses a carrier fluid with it to form a liquid droplet containing the particle. The droplet may then be dispensed to a microtiter plate, such that each well in the titer plate may contain a single target particle. The system may be used to separate individual biological cells, such as T cells, B cells, stem cells, cancer cells and sperm cells for further manipulation.

18 Claims, 13 Drawing Sheets

MEMS-BASED SINGLE PARTICLE SEPARATION SYSTEM

CROSS REFERENCE TO RELATED APPLICATIONS

Not applicable.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particles passing by the MEMS device in a fluid stream.

In another example, a MEMS devices may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between samples, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

SUMMARY

One feature of the MEMS-based microfabricated particle sorting system is that the fluid may be confined to small, microfabricated channels formed in a semiconductor substrate throughout the sorting process. The particles, perhaps biological cells, remain in the gently flowing sample stream throughout the process. The MEMS device may be a valve which separates one or more target particles from other components of the sample stream. The MEMS device may redirect the particle flow from one channel into another channel, when a signal indicates that a target particle is present. This signal may be photons from a fluorescent tag which is affixed to the target particles and excited by laser illumination in an interrogation region upstream of the MEMS device. Thus, the MEMS device may be a particle or cell sorter operating on a fluid sample confined to a microfabricated fluidic channel, but using detection means similar to a FACS flow cytometer.

Because of the nature of the MEMS devices, the architecture affords the possibility of manipulating micro-scale particles, such as biological cells, while the cells are constantly immersed in the gently flowing fluid. Using the systems and methods disclosed here, these small valves may be used to prepare a fluid sample containing a single target cell. This target cell may be the subject of further downstream study or manipulation, and may be, for example, a tumor cell, a T-cell, a B-cell, a stem cell or a cancer cell.

The systems and methods disclosed here may make use of a microfabricated MEMS fluidic valve in association with a fluidic interposer to form to form a MEMS-based single particle separation device. The MEMS-based separation device may separate one or more target particles from non-target material in a fluid stream, and output the target particle in a discrete quantity of fluid, for example, in an individual droplet.

The particle separation system may include a plurality of microfluidic channels, including a sample inlet channel and a sort channel, through which a sample fluid flows wherein the sample fluid contains one or more target particles and non-target material. Within the sample inlet channel may be an interrogation region disposed in the sample inlet channel, wherein the one or more target particles are distinguished from non-target material in the fluid stream. A microfabricated fluidic valve may be configured to separate the one or more target particles within the fluid stream. A carrier fluid inlet may supply a carrier fluid, to surround the one or more target particles with a quantity of carrier fluid. The quantity of carrier fluid, which now contains the separated, single particle, may be dispensed discretely by an outlet onto a receptacle. The receptacle may contain individual regions for storing the discrete quantities of fluids in an indexed fashion, such that a particular quantity of fluid may be stored in a known, particular location, separate from other quantities of fluid.

The method for separating one or more target particles from a sample stream, may include providing a microfabricated fluidic valve configured to separate the one or more target particles into one of a plurality of microfluidic channels. The method may then add a quantity of a carrier fluid to at least one of the microfluidic channels, to surround the one or more target particles with a quantity of carrier fluid. A discrete quantity of carrier fluid and the one or more target particles may then be dispensed onto a receptacle. The method may further include moving the receptacle to a new position to receive another discrete quantity of fluid containing one or more different target particles.

The MEMS-based single particle separation device may make use of a particular MEMS valve that has at least one of the microfabricated fluidic channel route the flow out of the plane of fabrication of the microfabricated valve. Such a valve may have a leak rate sufficient to provide adequate droplet volumes without the need for separate channels and valves.

The MEMS valve may include a microfabricated, movable member having a first diverting surface, wherein the movable member may move from a first position to a second position in response to a force applied to the movable member. The motion of the movable member may be substantially in a plane parallel to the surface, a sample inlet channel formed in the substrate and through which a fluid flows, the fluid including at least one target particle and non-target material. The flow in the sample inlet channel may be substantially parallel to the surface. The movable member may divert the fluid into a plurality of output channels wherein the flow in at least one of the output channels is not parallel to the plane, wherein at least one output channel is located directly below at least a portion of the diverting surface over at least a portion of its motion.

The target particle may be separated by this MEMS valve into a sort channel that may combine the particle with a carrier fluid. The separation device may then add a sufficient quantity of a carrier fluid to form a liquid droplet. The target particle in the carrier fluid may form a droplet at the end of the sort channel, at which point a tapered region forms a dropper for the system. When the droplet including the target particle falls from the dropper, it may be collected in a titer plate, or more particularly, in a microtiter plate, having a plurality of small fluid wells or reservoirs to contain a plurality of such droplets, each in a separate, indexed well. The microtiter plate may be positioned by a robot, in order to collect a particular target particle in a known, indexed, locatable well.

These and other features and advantages are described in, or are apparent from, the following detailed description.

BRIEF DESCRIPTION OF THE DRAWINGS

Various exemplary details are described with reference to the following figures, wherein.

DETAILED DESCRIPTION

The systems and methods describe a particle separation system which is capable of isolating a single target particle in a fluid droplet for further manipulation or study. The MEMS-based particle separation system may make use of a particular type of MEMS valve, but the particle separation system may make use of other designs of MEMS valves as well, and is not limited to any particular design of microfabricated valve.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation. The terms "sort" and "separate" are used interchangeably herein, to refer to the isolation of a target particle from non-target material flowing in a fluid stream. It should also be understood that the designations "sort" and "waste" are interchangeable, as they only refer to different populations of particles, and which population is called the "target" or "sort" population is arbitrary. It should also be understood that for ease of depiction, some drawings may not include all possible features and options, and that considerable simplification may be used in the illustrations of the actual methods, devices and systems.

Figure 1:
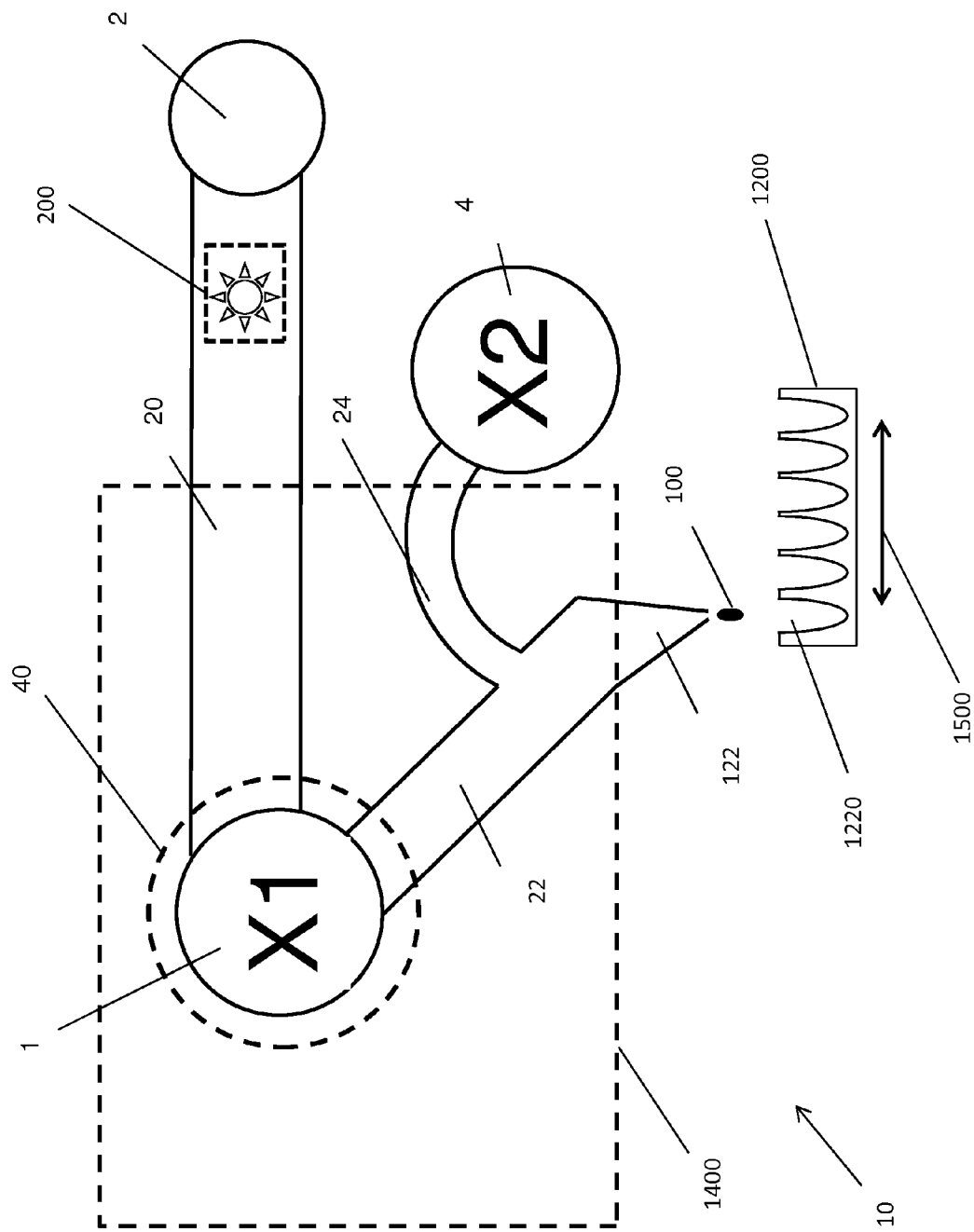
FIG. 1 is a simplified conceptual illustration of a first exemplary embodiment of a MEMS particle separation device configured to separate a single particle.

FIG. 1 is a simplified conceptual illustration of a first embodiment of a single cell separation device which may sort, separate or isolate a single target particle from the remainder of a fluid stream. After sorting or separation, an individual cell or target particle which is isolated by such a device may have around it on the order of a picoliter or even a femtoliter of fluid, an amount too small to be conveniently handled. The systems and methods disclosed here may add a quantity of "carrier" fluid to the cell as suspending and handling fluid, in order to form a discrete fluid quantity such as a droplet or such other amount as to be dispensable, that contains the target cell or particle. After the fluid is added, the single cell, now encased in a quantity of carrier fluid, can be launched into an appropriately sized vessel for storage prior to downstream processing or manipulation. The dispense of the carrier fluid and target cell may be done discretely, i.e. as a fluid of finite quantity, such as in droplets rather than a continuous flow, with each discrete quantity being stored in a different indexed receptacle. More generally, a plurality of discrete quantities of carrier fluid with one or more target particles contained therein may be dispensed by output structure 122 onto a receptacle, or into at least one of a plurality of fluid wells disposed in the receptacle.

In the embodiment shown in FIG. 1, the carrier fluid inlet 24 is coupled to the sort channel 22, and disposed downstream of the microfabricated fluidic valve 1. In this embodiment, the quantity of carrier fluid may be dispensed as a droplet into an appropriate, indexed receptacle. An indexed receptacle should be understood to mean a receptacle with a plurality of known locations, which can be repeatedly accessed to store the quantity of fluid. An example of an appropriate receptacle may be an indexed titer plate or microtiter plate with a plurality of wells for containing the fluid. The titer plate may thereby store individual quantities of fluids in an indexed fashion, such that a particular quantity of fluid is contained in a known, particular location. In this embodiment, the titer plate or microtiter plate 1200, may have a plurality of wells 1220 formed therein. The wells 1220 may be configured to hold about 1-100 microliters (ul) of fluid, such that they can comfortably hold the appropriate amount of material, which may range from less than 1 ul to 100 ul. For example, a single droplet may be 15-30 ul of volume. The microtiter plate 1200 may be moved as shown by a robot means 1500. Robot means 1500 may be an actuated and/or articulated positioner that is capable of repeatably positioning microtiter plate 1200. Robot means 1500 may have closed loop, feedback control to position microtiter plate 1200 accurately and repeatably, such that any of the plurality of wells 1220 of microtiter plate 1200 may be positioned under the output dropper structure 122. The robot means 1500 may index the microtiter plate 1200 such that a series of wells 1220 is positioned below a tapered dropper 122 formed in the MEMS-based single particle separation device 10. It should be understood that tapered dropper structure 122 is an exemplary embodiment, and that other sorts of output mechanisms may be provided to dispense the carrier fluid containing the single particle. Each droplet of fluid 100 may contain a single target particle which is separated from non-target material by the MEMS-based single particle separation device 10. Alternatively, the droplet 100 may contain a plurality of target particles, but little or no non-target material or non-target particles.

The MEMS-based single particle separation device 10 may include a input sort channel 20 which carries an input sample from a sample reservoir 2 to microfabricated, MEMS movable valve or actuator 1. The valve or actuator 1 may be capable of motion that closes off one microfabricated fluid channel and opens another. In the embodiment shown in FIG. 1, the MEMS valve 1 closes off a waste channel 40 that normally routes the input fluid into a waste channel which is perpendicular to the paper. This channel is indicated as the circular dashed line 40 in FIG. 1. It should be understood that this orifice need not be circular, but the aperture to waste channel 40 may have any arbitrary or complex shape. The channels 20, 22 and 40 may have dimensions on the order of 20-50 um, and the fluid may flow at a rate of about 4 ml/hour through these channels.

The input sample stream 20 may comprise particles, such as biological material or cells, which are suspended in a suitable fluid. The fluid may be, for example, buffer fluid, saline, water, blood, plasma, etc. The concentration of target cells in the fluid may be anywhere from about 10,000/ml to about $1 \times 10^6$/ml. The target particles may be for example, B-cells, T-cells, cancer cells, tumor cells, sperm cells, etc. The target particles may exist in the broader population of cells or particles in a wide range of frequencies, from common (1 in 10 perhaps) or even in the majority or even pure, to exceedingly rare (1 in 1 million or more). The channels may have dimensions chosen to accommodate the passage of biological cells having a diameter of on the order of 5-20 microns, being large enough to reduce clogging but small enough to encourage single-file passage of the cells through the channels.

An interrogation region 200 may exist in the input fluid channel 20. The interrogation region 200 is a region in input sample stream 20 wherein a target particle is distinguished from non-target material. Examples of suitable distinguishing mechanisms for interrogation region 200 will be described in further detail below, and may include laser interrogation of a fluorescent tag, for example, although other mechanisms may also be used.

Upon receiving the signal from interrogation region 200, the MEMS valve 1 may redirect the flow from the sample inlet reservoir 2 and input sample stream 20 to the single particle output stream 22. The MEMS valve 1 is designated "X1" in FIG. 1 to distinguish it from carrier fluid valve X2. The MEMS valve 1 may move in about 20-50 usecs from the first position to the second position, and may simultaneously close the aperture to the waste channel 40 and open the aperture to the single particle output channel 22. The MEMS valve 1 may remain in this second position for about 20-50 usecs, allowing a single target particle to flow into the sort channel 22, along with its associated fluid. According, at the fluid flow rates described above, the opening of MEMS valve 1 may introduce an exceedingly small quantity of fluid, on the order of picoliters, into single cell output channel 22.

In order to provide enough fluid to handle the single particle, a carrier fluid channel 24 may also be provided. This carrier fluid channel 24 may route a carrier fluid from a carrier fluid reservoir 4 to the sort channel 22. The carrier fluid may be, for example, a buffer fluid, a sheath fluid, a saline or medium, for example. The carrier fluid may be the same as the suspending fluid, or it may be different. A function of the carrier fluid is to provide sufficient fluid volume to transport and maintain the target cell in the microtiter plate 1200 well 1220. The carrier fluid may also contain active ingredients, such as growth inhibitors or promoters, nutritional compounds, antibiotic agents, antiviral agents, etc.

The carrier fluid may be dispensed from carrier fluid reservoir 4 through another valve shown as the "X2" in FIG. 1. This valve X2 may be a macroscopic valve, such as a solenoid or ball valve, or it may also be a microfabricated valve such as X1, or similar to MEMS valve 1. The carrier fluid is allowed to flow through valve X2 from carrier fluid reservoir 4 through carrier fluid channel 24, and into channel sort output channel 22 until it joins the target particle and forms a droplet 100 in the dropper 122 at the end of sort channel 22. Upon reaching sufficient size and weight, the droplet 100 may be dispensed into a well 1220 of microtiter plate 1200.

Because the MEMS valve 1 may be quite small, on the order of a few hundred microns, and the microtiter plate has macroscopic dimension, for example 3 cm×8 cm, it may be convenient to hold the MEMS valve 1 in an interposer 1400 which is designed to span the dimensions between the microscopic features of MEMS valve 1 and the macroscopic wells of the microtiter plate 1200. Interposer 1400 may provide this function, and is described in greater detail below with respect to FIGS. 10, 11, 12a, and 12b.

Figure 2:
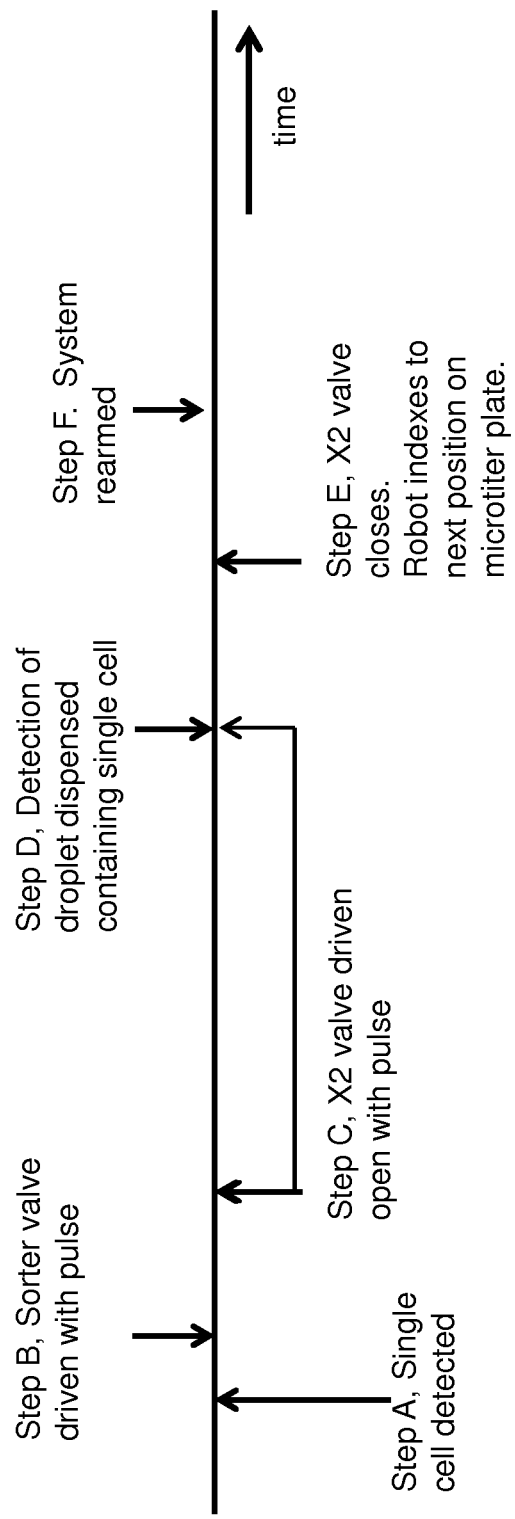
FIG. 2 is a view of a simplified timeline for controlling the microfabricated single particle separation system of FIG. 1 to dispense a droplet containing the single particle.

A simplified timing diagram is shown in FIG. 2, which illustrates the timing of events associated with the separation of a single target particle from the fluid stream by MEMS-based particle separation system 10. As shown in FIG. 2, the process begins with the detection of a single target cell in the interrogation region 200, in step A. In step B, upon detection of the target particle, a pulse is sent to MEMS valve 1, causing it to move from the first to the second position, closing off waste channel 40 and opening sort channel 22. A signal may also be sent to a robot controlling the position of the microtiter plate 1200, causing it to move a well 1220 into position under the dropper structure 122, that is, to the position of an indexed well location. In step C, the carrier fluid valve X2 may be opened, such that a droplet 100 begins to develop which will contain the target particle. Upon reaching the requisite volume, the droplet 100 falls from dropper structure 122. Upon detection that the droplet has been dispensed in step D, the robot may move the microtiter plate 1200 to a new, indexed position in step E, to receive another quantity of fluid containing one or more different target particles. The system may be rearmed in step F.

Exemplary durations in the timeline of FIG. 2 are:
Time between step A and step B: 20 usecs
Time between step B and step C: 10 usecs-10 msecs
Duration step C: 10-100 msecs
Time between step D and step E: 10 msecs
Time between step E and step F: 10 msecs Accordingly, it should be understood that the spatial intervals shown in FIG. 2 are not necessarily proportional to the time elapsing between the various steps. Furthermore, it should be understood that these intervals are exemplary only, and that these details will depend upon the application and hardware used. For example, the duration of step C will depend on the pressure used in the carrier fluid channel 24. It should also be understood that the method used may be far more complex than that shown in FIG. 2. Steps such as measuring the droplet size, closing valves X1 and X2, as well as many others, are implicit, but not mentioned in the interest of simplicity and clarity of the figure.

The valve X2 used to control the flow of carrier fluid may be quite slow, taking 10 msec or more to open or close, and the robotic movements may be similarly slow, on the order of msecs. Another option may be to not use a valve X2 at all, but instead to allow the carrier fluid to flow at a constant rate in to the sort channel 22. Droplets may be formed passively and at a constant rate as a passive sheath flow. These droplets will not, in general, contain a target particle and may simply be stored in a waste receptacle or discarded. This embodiment is described below with respect to FIG. 3.

Figure 3:
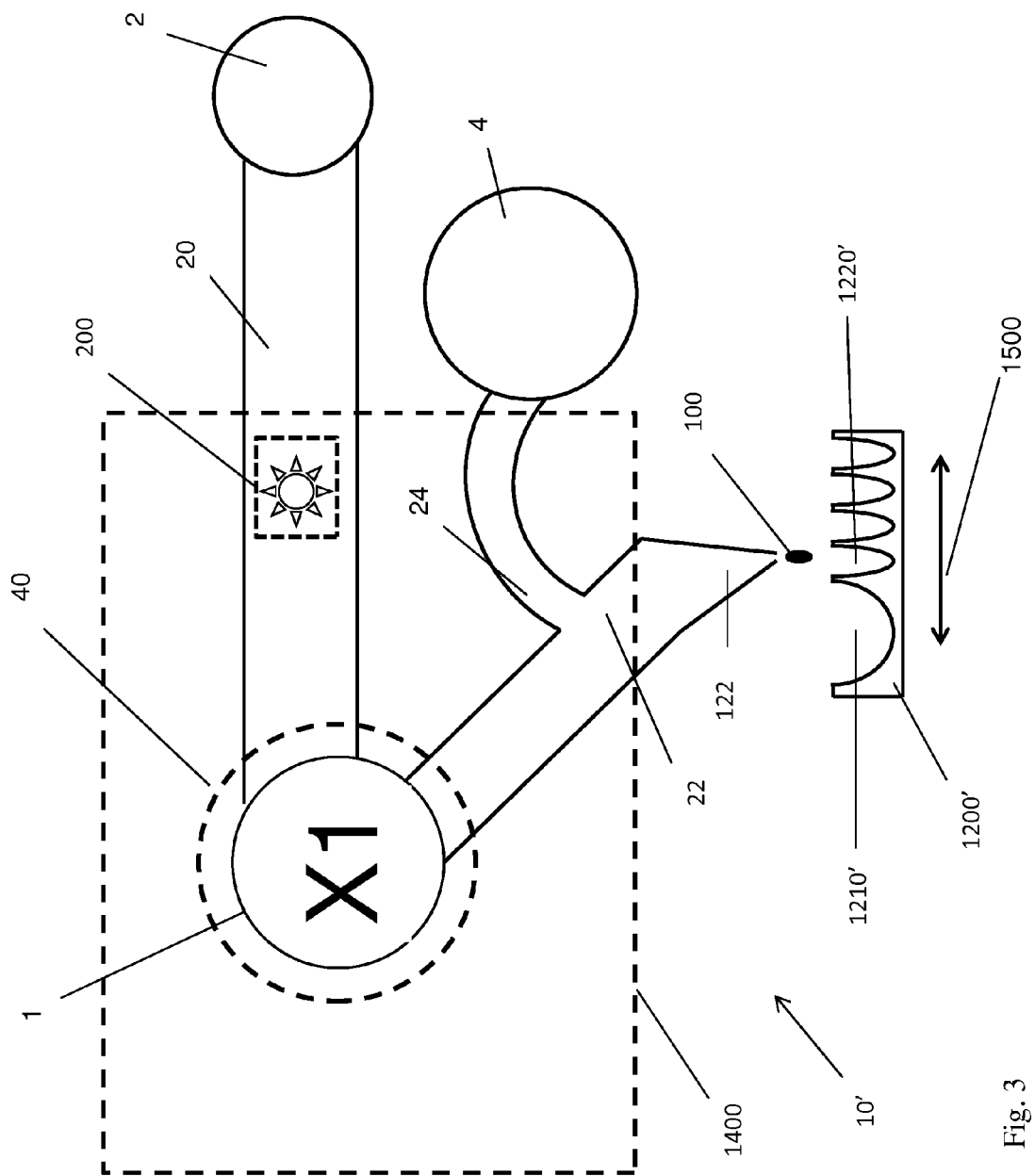
FIG. 3 is a simplified conceptual illustration of a second exemplary embodiment of a MEMS particle separation device configured to separate a single particle.

FIG. 3 is a simplified conceptual illustration of a second embodiment of a MEMS-based single cell separation device 10' which may sort, separate or isolate a single target particle from the remainder of a fluid stream. This embodiment 10' is similar to that shown in FIG. 1, except that the carrier fluid flow is not controlled by a valve, but is simply allowed to flow continuously. Because of this constant flow, droplets may be emitted continuously by the dropper structure 122. A second sort of microtiter plate 1200' may have a larger reservoir 1210' to contain these "empty" droplets. The robot may maintain the position of this waste reservoir 1210' under the dropper structure 122, until a target particle is detected in interrogation region 200.

Figure 5:
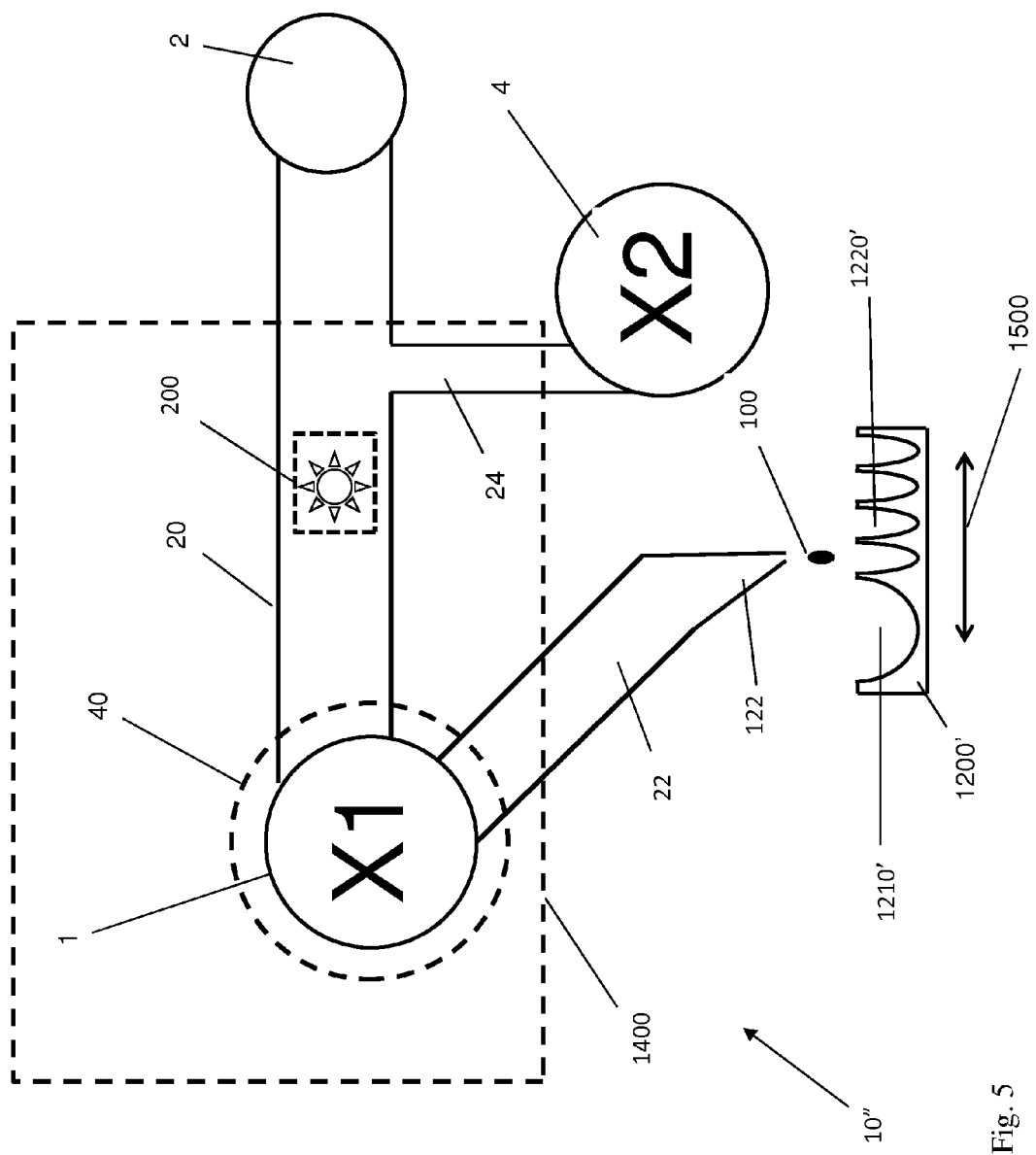
FIG. 5 is a simplified conceptual illustration of a third exemplary embodiment of a MEMS particle separation device configured to separate a single particle.

In order to separate the droplet containing the single particle from the droplets that do not contain the target particle, a signal may be sent to the robot means 1500 controlling the positioning on microtiter plate 1200' informing it that a target particle has been detected. Upon receiving this signal, the robot means 1500 may shift the position of the microtiter plate 1200' to a position such that the forming droplet will be dropped into a smaller well 1220' rather than the larger waste well 1210'. Details of microtiter plate 1200 and microtiter plate 1200' are shown in FIGS. 6a, 6b, 7a and 7b. It should be understood that the depiction of microtiter plate 1200, interposer 1400 and MEMS valve 1 in FIGS. 1, 3 and 5 are not necessarily to scale, and microtiter plate 1200 and interposer 1400 may appear on scale with MEMS valve 1 in order to show the features of each. In reality, MEMS valve 1 may be much smaller relative to microtiter plate 1200 and interposer 1400.

Figure 4:
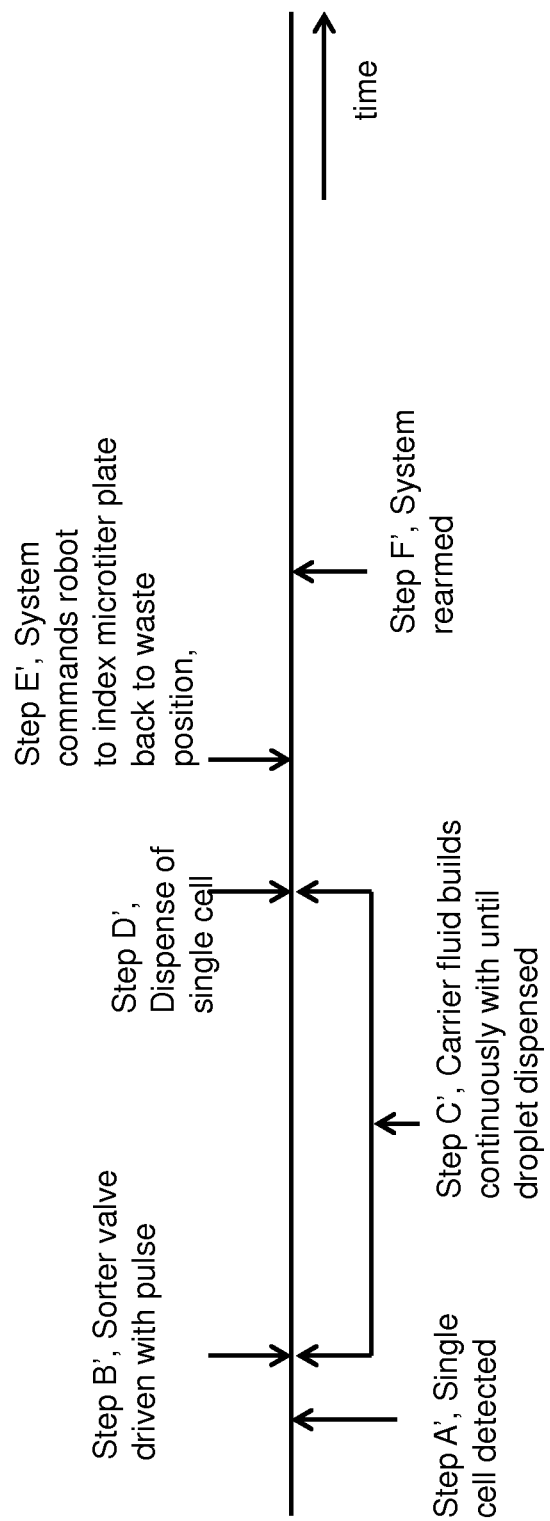
FIG. 4 is a view of a simplified timeline for controlling the microfabricated single particle separation device of FIG. 1 to dispense a droplet containing the single particle.

A simplified timing diagram is shown in FIG. 4, which illustrates the timing of events associated with the separation of a single target particle from the fluid stream by MEMS-based particle separation system shown in FIG. 3. As in the prior method, the process begins with the detection of a single target cell in the interrogation region 200, in step A'. In step B', upon detection of the target particle, a pulse is sent to MEMS valve 1, causing it to move from the first to the second position, closing off waste channel 40 and opening sort channel 22. A signal may also be sent to a robot means 1500 controlling the position of the microtiter plate 1200, causing it to move a well 1220' into position under the dropper structure 122. That is, the robot means 1500 may be commanded to move microtiter plate 1200' such that a small volume, indexed well location 1220' is positioned under dropper structure 122 rather than the larger waste well 1210'. Because no valve X2 is used in this embodiment, step C', requires only that time elapse while the carrier fluid flows. The fluid builds continuously until a droplet is dispensed. Upon detection that the droplet has been dispensed in step D', the robot means 1500 may move the microtiter plate 1200' to a new location in step E'. The system may be rearmed in step F'.

Because of the slow movements of valve X2 and robotic actuator moving microtiter plate 1200, the motions may be invoked earlier, and in anticipation of an event. That is, because the approximate length of time required for droplet formation is known, as is the activation of MEMS valve 1, the robotic means 1500 may be activated before the droplet is formed and ready to drop.

Exemplary durations in the timeline of FIG. 4 are:
Time between step A' and step B': 20 usecs
Time between step B' and step C': 10 usecs-10 msecs
Duration step C': 10-100 msecs
Time between step D' and step E': 10 msecs
Time between step E' and step F': 10 msecs As before, it should be understood that the spatial intervals shown in FIG. 4 are not necessarily proportional to the time elapsing between the various steps. The intervals shown are exemplary only, and these details will depend upon the application and hardware used. For example, the duration of step C' will depend on the pressure used in the carrier fluid line. It should also be understood that the robot means 1500 may be moved at times other than the point shown in FIGS. 2 and 4. For example, upon notification that the MEMS valve 1 has been activated and a target particle has been separated, the microtiter plate 1200 or 1200' may be moved into position. As with the timeline shown in FIG. 2, it should be appreciated that many more steps may exist than those shown in the figures, which are limited to five for the sake of clarity.

FIG. 5 is a simplified conceptual illustration of a third embodiment of a MEMS-based single cell separation device 10" which may sort, separate or isolate a single target particle from the remainder of a fluid stream. This embodiment 10" is similar to that shown in FIG. 1, except that the carrier fluid input is located upstream of MEMS valve 1 rather than downstream as in the first two embodiments. The carrier fluid input from carrier fluid input reservoir 4 may be equipped with a valve X2 as shown. If there is no need to control the flow, it may flow continuously without a valve as with the previous embodiment. Because the embodiment 10" shown in FIG. 5 may not use an additional valve X2 or an additional channel 24, this embodiment 10" may be used when consumption of fluid materials is not an issue because of cost or availability, or when ease of implementation is important. This embodiment 10" resembles the injection of a sheath flow in other particle sorting systems, which may occur upstream of the sorting device, and may consume tens of ml of fluid, as the carrier fluid is flowing constantly.

This embodiment may be used when the MEMS valve 1 is sufficiently leaky that enough fluid flows around the device to generate a droplet at a reasonable rate at the dropper structure 122. That is, the droplet formation rate may be determined by the volume of sorted material in addition to the leak rate around MEMS valve 1. Accordingly, this embodiment may be particularly appropriate for use with the MEMS valves shown in detail in FIGS. 8 and 9.

Figure 6:
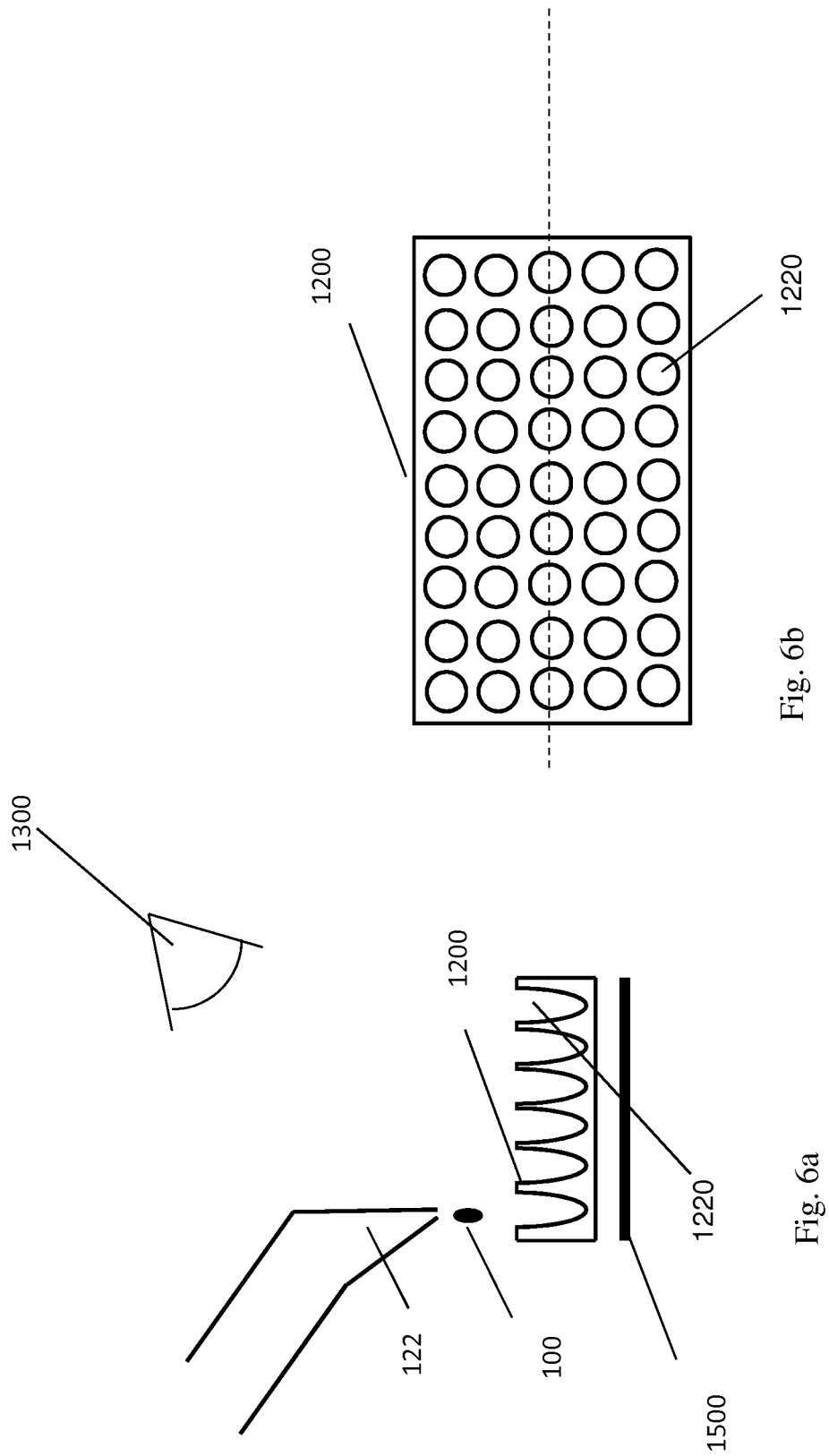
FIG. 6*a* is a cross sectional view of a microtiter plate having a plurality of substantially identical fluid wells.
FIG. 6*b* is a plan view of the microtiter plate of FIG. 6*a*.

FIGS. 6a and 6b illustrate further detail of the microtiter plate 1200. It should be understood that microtiter plate 1200 is only one exemplary embodiment, and that any other receptacle may be used to receive the separated single particles 100. Appropriate receptacles may have dedicated, indexed, separate regions formed therein, for storing separate quantities of fluid. For example, microtiter plate 1200 may consist of an array of depressions or wells formed therein, which can each receive and store a quantity of fluid. The microtiter plate 1200 is shown in cross section in FIG. 6a, and plan view in FIG. 6b. Although 50 wells 1220 are shown in FIG. 6b, it should be understood that this is for ease of depiction, and in reality, there may be far more.

The wells may be dimensioned to comfortably hold about 1-100 ul of fluid, in order to hold a droplet 100 having a fluid volume of 1-100 ul, for example. The pitch between the wells can vary by several orders of magnitude, for example between about 50 microns and about 5 mm. It should be understood that these dimensions are exemplary only, and that such details may depend on the circumstances of the application. The microtiter plate 1200 may be made from a bio-compatible plastic, and may be made by injection molding with intermediate tolerances of +/−10 um. As shown in FIGS. 6a and 6b, in microtiter plate 1200, all wells are approximately of the same shape and size, and are indexed so that microtiter plate 1200 may be moved by a robot means 1500 in the direction shown in FIG. 1, 3 or 5. This may position any one of the 50 wells or depressions 1220 under the dropper 122. Detection system 1300 will be discussed in more detail below.

Figure 7:
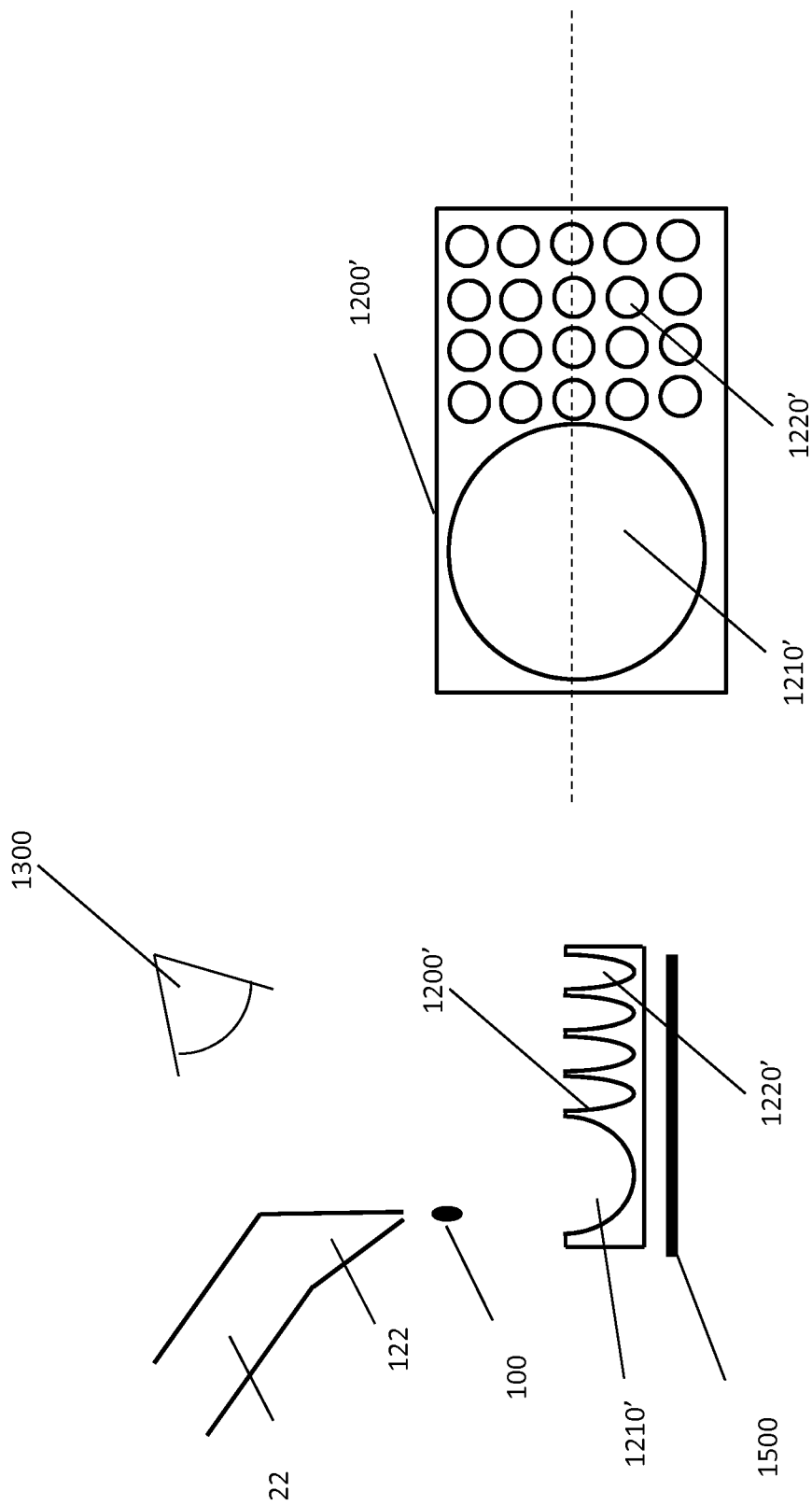
FIG. 7*a* is a cross sectional view of a microtiter plate having a plurality of non-identical fluid wells.
FIG. 7*b* is a plan view of the microtiter plate of FIG. 7*a*.

FIGS. 7a and 7b illustrate further detail of the microtiter plate 1200'. Like microtitier plate 1200, microtiter plate 1200' may consist of an array of depressions or wells formed therein, which can receive a quantity of fluid. The microtiter plate 1200 is shown in cross section in FIG. 7a, and plan view in FIG. 7b. As can be seen, microtiter plate 1200' may have wells or depressions of different sizes, capable of holding different volumes of fluids. In the embodiment shown in FIG. 7a, in addition to the smaller sized depressions 1220', a single large depression 1210' may be provided in microtiter plate 1200'. This large depression may be capable of holding a larger quantity of fluid, and thus may be appropriate for storing the multiple droplets that do not contain a target particle. This is the situation, for example, in the second embodiment of MEMS-based separation system 10, shown in FIG. 3.

A technical matter may arise, which is how to detect that the droplet 100 has been released from the dropper 122 and fallen into the microtiter plate 1200'. A plurality of techniques may be used to determine whether the droplet 100 has fallen. The techniques may include measuring weight changes, vibration, or direct optical imaging, to name just a few. The detection system is shown generically as optical imager 1300 in FIGS. 6a and 7a. However, it should be understood that this embodiment is exemplary only, and that other techniques may be used to determine if and when the droplet 100 has been released.

It should also be understood that the droplet may be transferred to the microtiter plate 1200' by blotting rather than dropping, that is, by relying on meniscus forces rather than gravity to transfer the droplet 100 to the microtiter plate 1200'. In this embodiment, the microtiter plate 1200' may be raised vertically by the robot means 1500 until the droplet 100 touches a surface of the microtiter plate 1200'. At this point, meniscus forces acting on the droplet 100 may encourage the wicking of the droplet 100 from the dropper 122 into the microtiter plate 1200 or 1200'. Completion of the transfer may be confirmed by any of the techniques mentioned above.

It may also be possible to shake the components MEMS valve 10 and/or interposer 1400 to release the droplet 100 to the microtiter plate 1200. In this embodiment, MEMS valve 1 may be mounted on a vibration stage (not shown) and vibrated to encourage the release of the droplet. The frequency of vibration may be chosen to be outside of those which would interfere with the detection apparatus associated with interrogation region 200.

Figure 8:
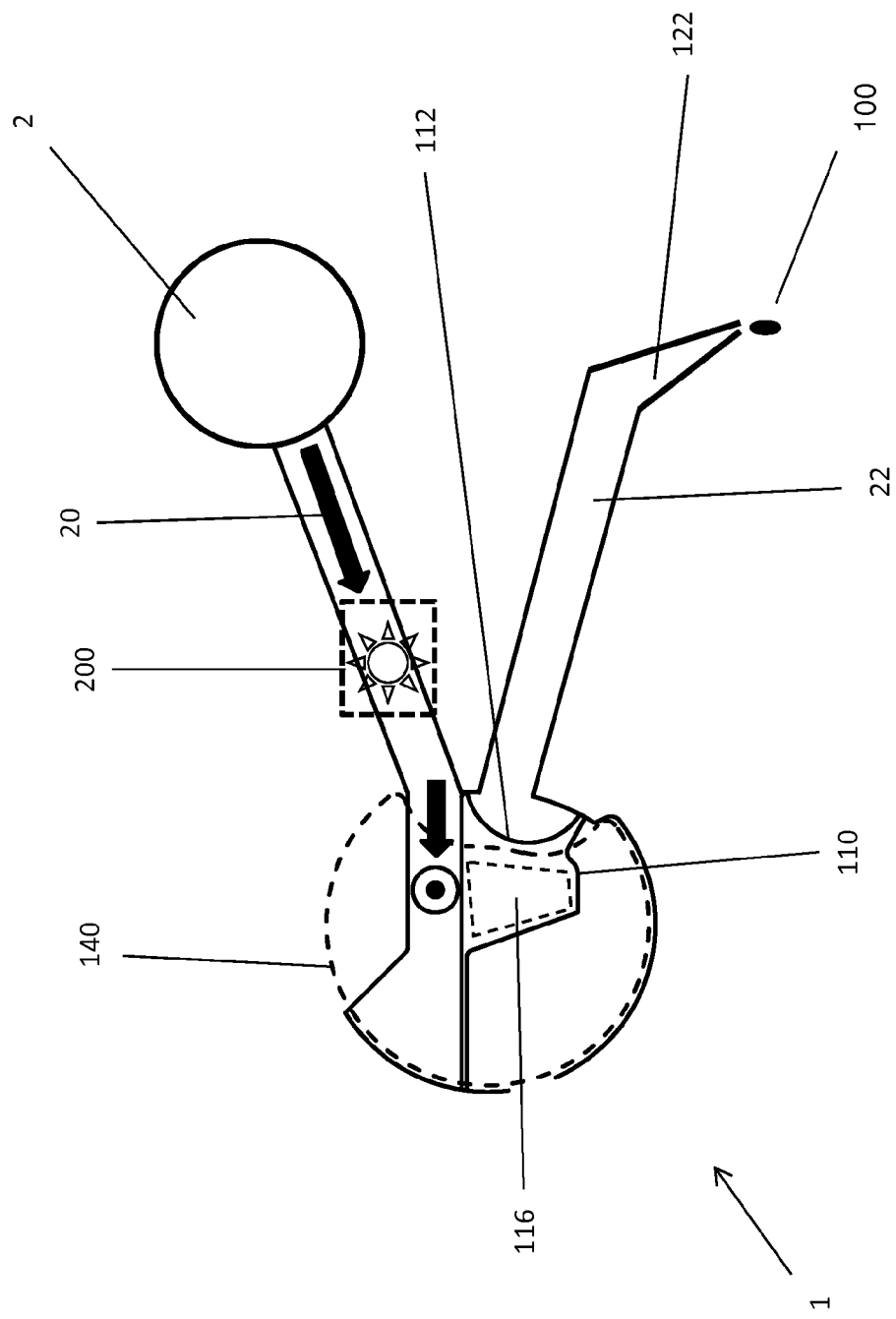
FIG. 8 is a plan view of a MEMS particle sorting valve, which can be used to separate single particles in the MEMS particle separation devices shown in FIGS. 1, 3 and 5, with the valve in the unactuated (waste) position.

FIG. 8 is a schematic diagram of a microfabricated cell sorting mechanism, MEMS valve 1, which may be used in the particle separation systems 10, 10' and 10" described here. Details of MEMS valve 1 and its manufacture may be found in co-pending U.S. patent application Ser. No. 13/998,095, (hereinafter the '095 patent application) filed Oct. 1, 2013 and incorporated by reference herein. Among the unique features of MEMS valve 1 is that the motion of the cell sorting valve 110 is parallel to the fabrication plane of the valve. In addition, the waste channel 140 is substantially orthogonal to the sample inlet channel 20 and the sort output channel 22, and orthogonal to this plane. These features enable distinct advantages in terms of speed and precision, valve throughput and ease of the microfluidic sorting. The sort channel 22 may lead to a tapered dropper structure 122 from which drops 100 may form, In the plan view illustration of FIG. 8, the novel MEMS valve 1 is in the quiescent (un-actuated) position. The MEMS valve 1 may include a microfabricated fluidic valve or movable structure 110 and a number of microfabricated fluidic channels 20, 22 and 140. The fluidic movable structure 110 and microfabricated fluidic channels 20, 22 and 140 may be formed in a suitable substrate, such as a silicon substrate, using MEMS lithographic fabrication techniques as described in greater detail in the '095 application. The fabrication substrate may have a fabrication plane in which the device is formed and in which the movable member 110 moves.

A sample stream may be introduced to the microfabricated fluidic movable structure 110 by a sample inlet channel 20 via the interposer 1400 described below. The sample fluid may be stored in a sample reservoir 2 in a removable cartridge, also described below, prior to sorting by fluidic movable structure 110. The sample fluid may contain a mixture of particles, including at least one desired, target particle and a number of other undesired, non-target particles. The particles may be suspended in a diluting or buffer fluid or medium. For example, the target particle may be a biological material such as a stem cell, a cancer cell, a zygote, a protein, a T-cell, a bacteria, a component of blood, a DNA fragment, for example, suspended in a buffer fluid such as saline.

The inlet channel 20 may be formed in the same fabrication plane as the movable structure 110, such that the flow of the fluid is substantially in that plane. The motion of the movable structure 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Laser interrogation region 200 is the portion of the microfluidic passageway in which an illuminating or interrogating laser is directed on the target particle, in order to distinguish it from the other constituents of the fluid sample. Details as to this detection mechanism are well known in the literature. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an non-target particle and thus rejected or otherwise disposed of.

With the movable structure 110 in the position shown, the input stream passes unimpeded to an output orifice and channel 140 which is out of the plane of the inlet channel 20, and thus out of the fabrication plane of the MEMS valve 1. That is, the flow is from the inlet channel 20 to the output orifice 140, from which it flows substantially vertically, and thus orthogonally with respect to the inlet channel 20. This output orifice 140 leads to an out-of-plane channel that may be perpendicular to the plane of the paper showing FIG. 8. More generally, the output channel 140 is not parallel to at least one of the plane of the inlet channel 20 or sort channel 22, or the fabrication plane of the movable structure 110. Diverting surface 112 and permalloy inlaid material 116 on movable object 110 will be discussed below.

The output orifice 140 may be a hole formed in the fabrication substrate, or in a covering substrate that is bonded to the fabrication substrate. Further, the movable structure 110 may have a curved diverting surface 112 which can redirect the flow of the input stream into the sort output stream. The contour of the orifice 140 may be such that it overlaps some, but not all, of the inlet channel 20 and sort channel 22. By having the contour 140 overlap the inlet channel 20, a route exists for the input stream to flow directly into the waste orifice 140 when the movable structure or valve 110 is in the un-actuated waste position. The waste channel 140 may lead to a waste reservoir 40, which may collect the non-target material. Because of design and manufacturing tolerances associated with the fabrication of MEMS valve 1, leakage of the suspending fluid may also occur between the sample inlet channel 20 and the waste and sort channels 140 and 22, regardless of the position of the movable structure 110.

The characteristic size of MEMS valve 1 may be on the order of 300-400 microns across, with channels 50 microns deep and 25 microns wide. The aperture to the waste output orifice 140 may be about 50-100 microns wide.

Figure 9:
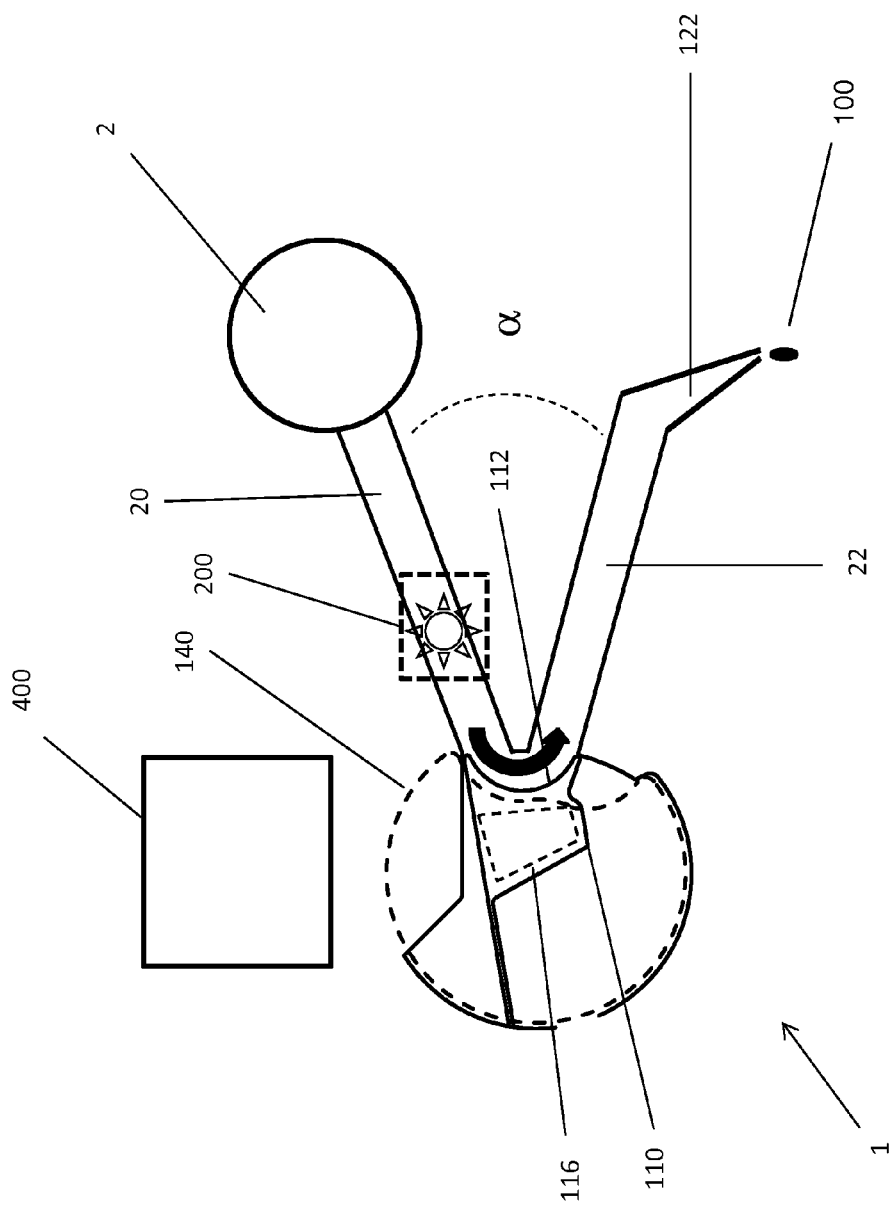
FIG. 9 is a plan view of a MEMS particle sorting valve, which can be used to separate single particles in the MEMS particle separation devices shown in FIGS. 1, 3 and 5, with the valve in the actuated (separate) position.

FIG. 9 is a plan view of the MEMS valve 1 in the actuated position. In this position, the movable structure 110 is deflected upward into the position shown in FIG. 9. The diverting surface 112 is a sorting contour which redirects the flow of the inlet channel 20 into the sort output channel 22. The output channel 22 may lie in substantially the same plane as the inlet channel 20, such that the flow within the sort channel 22 is also in substantially the same plane as the flow within the inlet channel 20. There may be an angle $\alpha$ between the inlet/channel 20 and the sort channel 22. This angle may be any value up to about 90 degrees. In one embodiment, the angle between inlet channel 20 and sort channel 22 is about 180 degrees, such that flow in the respective channels is essentially antiparallel.

Actuation of movable structure 110 may arise from a force generated by force-generating apparatus 400, shown generically in FIG. 9. In some embodiments, force-generating apparatus may be an electromagnet, as described below. However, it should be understood that force-generating apparatus may also be electrostatic, piezoelectric, or some other means to exert a force on movable structure 110, causing it to move from the first position (FIG. 8) to the second position (FIG. 9). The sort channel 22 may lead to the tapered dropper structure 122 from which drops may form.

In some embodiments, the force generating apparatus 400 may include coils which generate a magnetic field, which then interacts with the movable member. In order to make the movable member responsive to such an electromagnetic force, it may have a magnetically permeable material inlaid into movable structure 110. The extent of this material may be to the edge, but just inside, the outline of 110 shown in FIGS. 8 and 9.

A magnetically permeable material should be understood to mean any material which is capable of supporting the formation of a magnetic field within itself. In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ $H \cdot m^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000. Accordingly, movable valve 110 may have permalloy material inlaid 116 into the movable feature 110 and subsequently planarized so that the profile of the movable valve remains flat. Additional details as to the fabrication of such permeable features may be found in the incorporated '095 patent application.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux.

When the valve or movable member 110 is un-actuated as in FIG. 8, the flow of the inlet channel 20 may flow directly into the waste channel 140 by going over, around or by the movable member or valve 110. The area on top of the valve or movable member 110 may be relieved to provide clearance for this flow, and thus increase the leakage rate if desired. Thus, when the movable member is un-actuated, the flow will be sent directly to the waste channel. When the movable member is actuated, most of the fluid will be directed to the sort channel, although liquid may still flow over and under the movable member. The MEMS movable member 110 may leak in either position, such that the suspending fluid may leak into both the waste channel 140 as well as the sort channel 22 as a general rule, and this feature may be particularly useful in the embodiment shown in FIG. 5.

Figure 10:
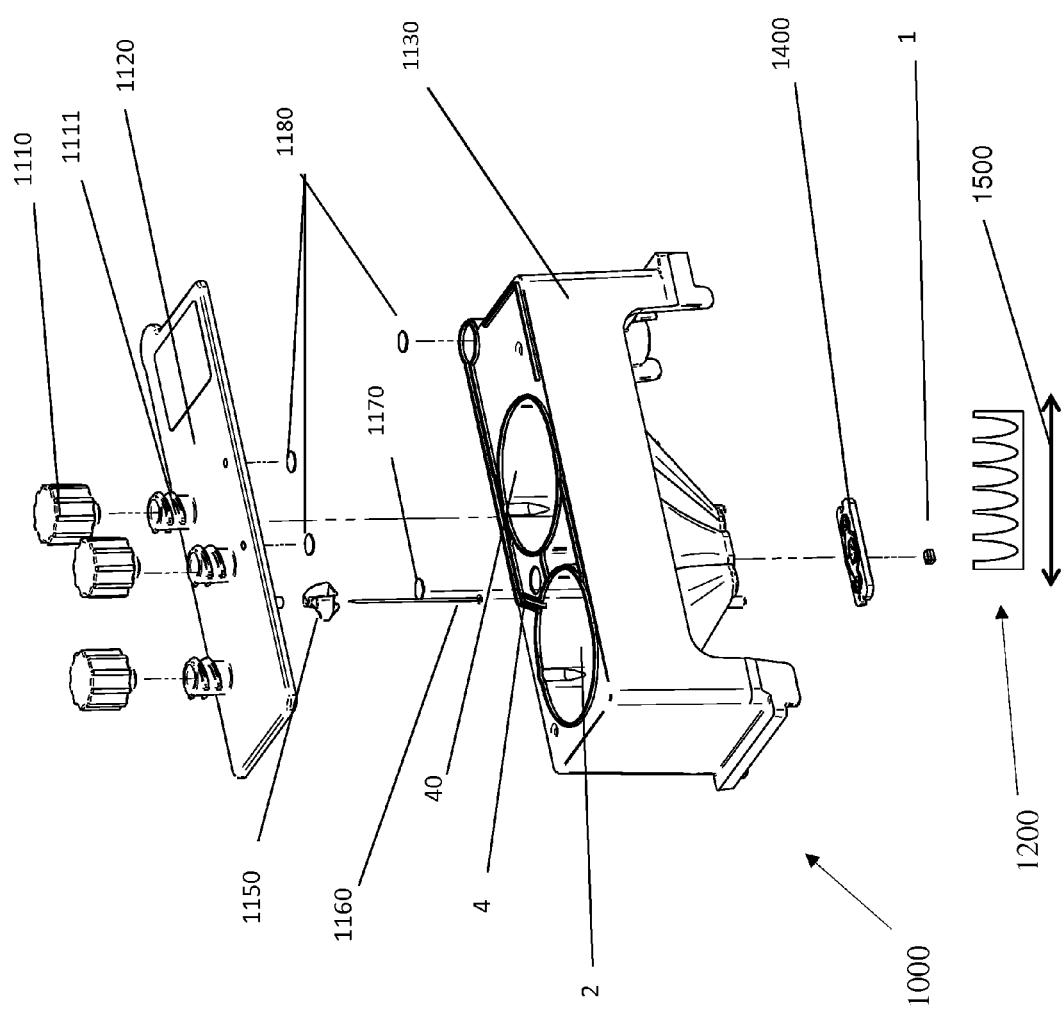
FIG. 10 is an exploded view of an exemplary cartridge and interposer which can be used with the MEMS particle separation device of FIG. 1, 3 or 5.

FIG. 10 is an exploded perspective view of an exemplary disposable cartridge 1000 which may be used in the particle sorting system which will be shown and described below with respect to FIG. 13. Disposable cartridge 1000 may include several assemblable pieces, such as top 1120 and base 1130. Disposable cartridge 1000 may hold the MEMS-based single particle separation device 10 which includes the MEMS valve 1, as well as the interposer 1400 further described below.

Disposable cartridge 1000 may also provide storage for the various fluids in fluid reservoirs which may be contained therein. Accordingly, the base 1130 of disposable cartridge 1000 may have a plurality of voids or compartments formed therein, including sample fluid reservoir 2, carrier fluid reservoir 4 and waste reservoir 40. As described further below, the sample to be sorted may be stored in sample reservoir 2, the carrier fluid in carrier reservoir 4 and waste effluent in waste reservoir 40. The fluidic passageways between these voids may all be disposed in the interposer 1400 and/or in the MEMS valve 1.

Between the top 1120 and the base 1130 may be disposed a number of filters 1180 to protect the sample from contamination or debris. These filters 1180 may be 20 micron Sterifilters, for example. The filters 1180 may be located directly above the various fluid reservoirs 2, 4 and 40.

Within the sample reservoir 2 and enclosed between the top 1120 and the base 1130 may be a magnetized propeller 1150, and a needle 1160 which may act as a shaft for magnetized propeller 1150. Upon exposure to a circulating magnetic field, magnetized propeller 1150 may rotate on shaft 1160, causing the contents of the sample reservoir 2 to be mixed or homogenized. Finally, a 0.20 micron filter 1170 may be placed over the carrier fluid reservoir 4, to protect the contents from contamination from the ambient environment.

Sample fluid may be introduced to the sample reservoir with a pipette, or with a syringe and plunger (not shown) through the access ports 1111 shown, whereupon the cartridge may be sealed with thumbscrews 1110. Alternatively, the cartridge may be delivered with the sample fluid already loaded therein. The microtiter plate 1200, or other receptacle, may be positioned under interposer 1400 and MEMS valve 1, as shown in FIG. 10. The output dropper may then dispense droplets into the receptacle 1200 as shown next in FIG. 11.

Figure 11:
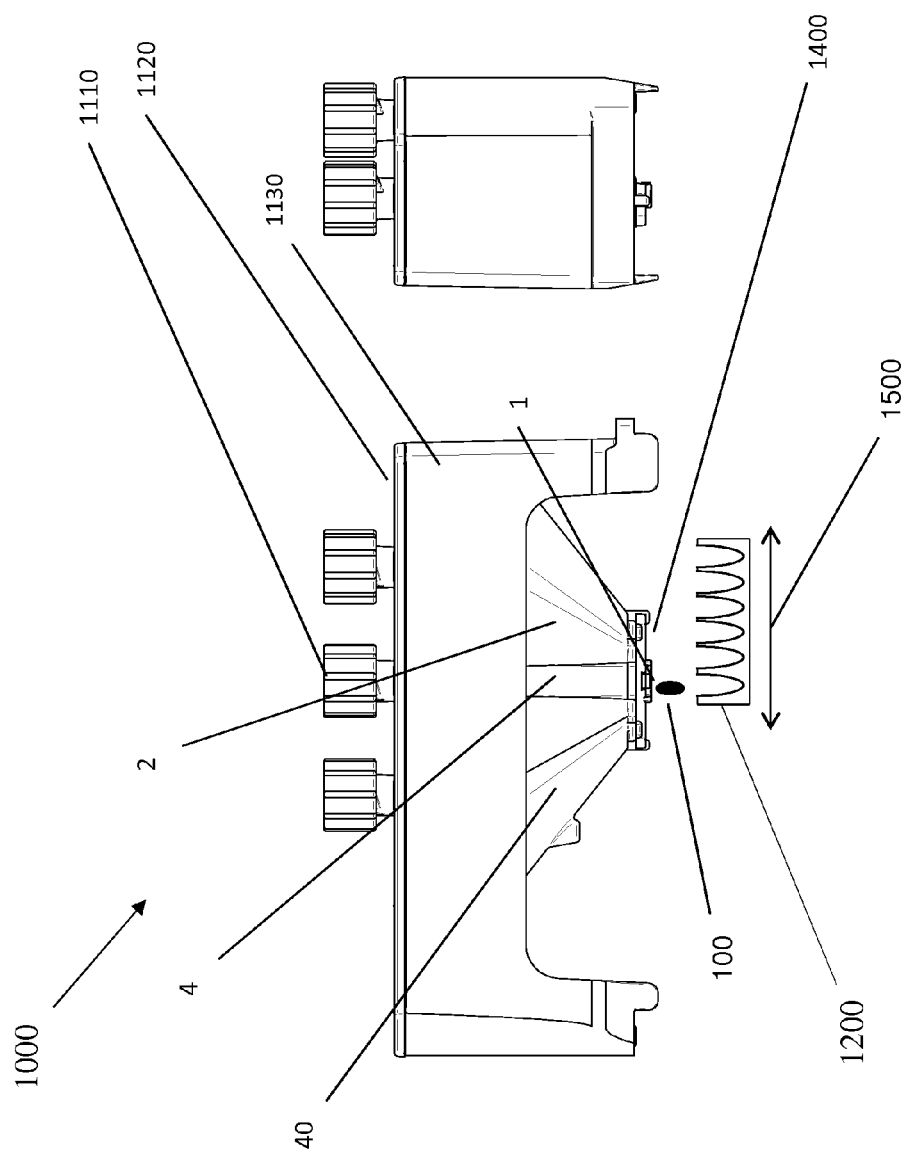
FIG. 11 is a side view of an exemplary cartridge and interposer which can be used in the MEMS particle separation device of FIG. 1, 3 or 5.
Figure 12:
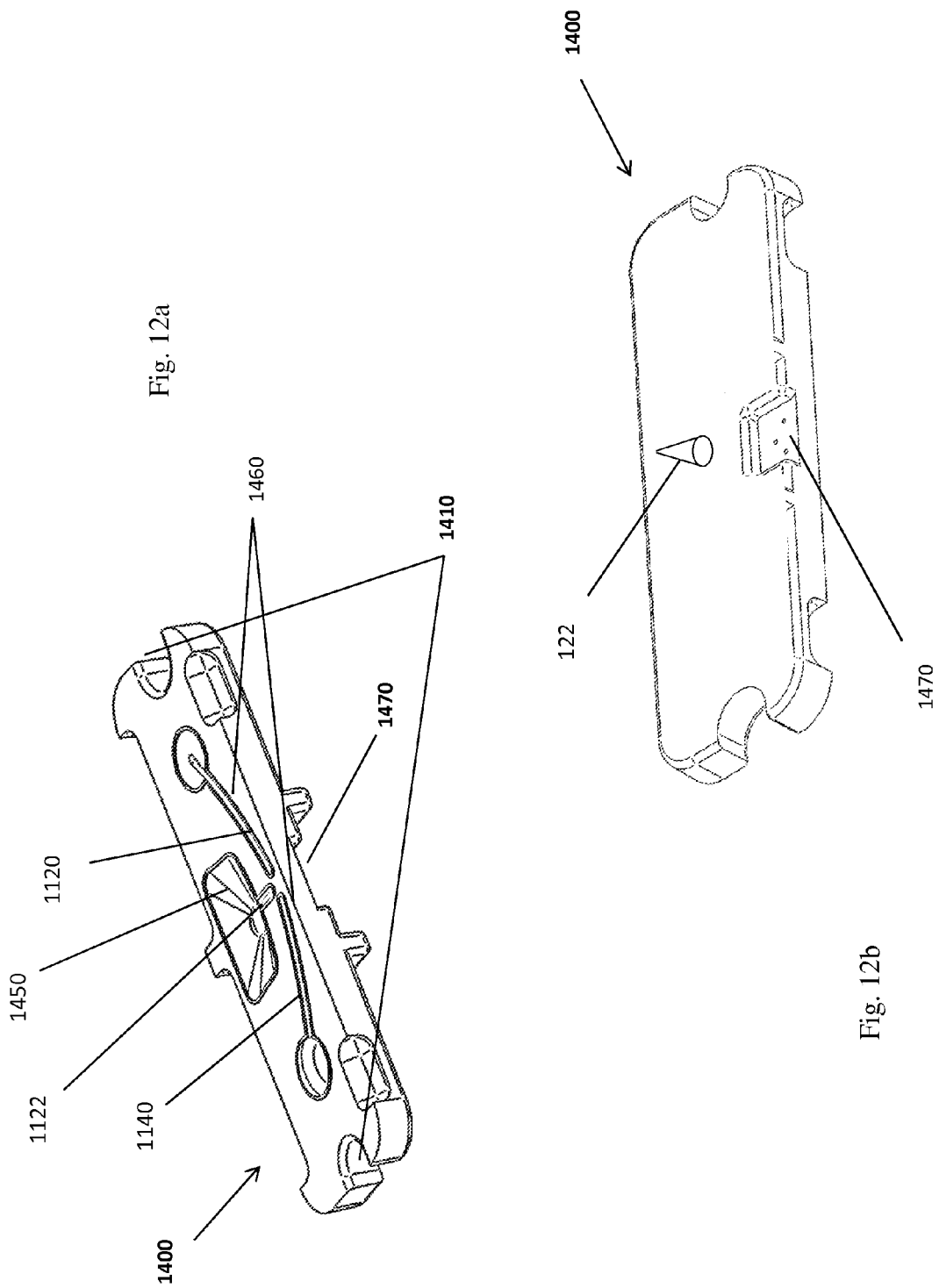
FIG. 12*a* is a perspective view of an exemplary interposer which can be used in the MEMS particle separation device of FIG. 1, 3 or 5.
FIG. 12*b* is the obverse side of the exemplary interposer of FIG. 12*a*.

FIG. 11 is a side view of the assembled disposable cartridge 1000, showing the sample fluid reservoir 2, carrier fluid reservoir 4 and waste reservoir 40. Shown in the assembled view are the relative locations of the MEMS valve 1 and interposer 1400 with respect to the cartridge base 1130. It should be noted that FIG. 11 is inverted compared to FIG. 10, such that the sample reservoir 2, shown on the left hand side of the cartridge in FIG. 10, is now located on the right hand side in FIG. 11, as are the associated channels, stirrer, etc. Also shown in FIG. 11 is the relative positioning of the titer plate receptacle 1200, and positioning thereof by robot 1500. It should be understood that FIG. 11 is not drawn to scale, as the appearance of single particle droplet 100 is shown much larger relative to the other components than it may actually be.

To provide a transition region between the very fine, microfabricated features of the MEMS valve 1 and the much larger fluid volumes of reservoirs 2, 4 and 40 in cartridge 1000, an interposer 1400 may be provided. The interposer 1400 may be formed from plastic by, for example, injection molding and may have intermediate tolerances on the order of +/−10 µm. The purpose of the interposer 1400 is to provide a transition between the very small structures of the MEMS valve 1 and the gross, macroscopic structures of the cartridge 1000 and reservoirs 2, 4 and 50, and to provide the dropper structure 122 for sort channel 22.

Because the interposer 1400 can be made with reasonably fine tolerances (+/−10 µm), it is possible to align the passages in the interposer 1400 with passages in the MEMS chip when the apertures to the interposer channels are on the order of about 300 microns. While the widths of the channels leading to and from the movable structure 110 may be substantially smaller on the order of 150 microns, the apertures which introduce the fluid to the channels may be made near this scale. The holes are shown in FIGS. 12a and 12b.

Accordingly, the interposer may have passages formed therein, 1120, 1122 and 1140, shown in FIG. 12a, which may correspond to channels 20, 22 and 140 of MEMS valve 1, shown in FIGS. 8 and 9. That is, passage 1120 may mate with passage 20 on MEMS valve 1, to provide a fluidic pathway from sample reservoir 2 to sample input channel 20 on MEMS valve 1. The interposer 1400 may also provide a fluidic pathway from the movable structure 110 to the carrier reservoir 4 (in cartridge) via carrier channel 24 (on chip and shown on FIGS. 1 and 3) and 1122 (on interposer). Similarly, the interposer 1400 may provide a fluidic pathway from the movable valve 110 to the waste reservoir 40 (in cartridge) via waste channel 140 (on chip and shown in FIGS. 8 and 9) and 1140 (on interposer).

Another purpose of the interposer is to provide the dropper structure 122 from relieved droplet region 1450, to dispense the droplets containing the single target particles. This droplet region 1450 is shown in FIG. 12b.

In particular, it should be noticed that the floor of droplet region 1450 is at a lower elevation than the bottom of the sort channel 1122. Accordingly, droplet 100 may flow as assisted by gravity and meniscus forces from the MEMS valve 1 to the dropper structure 122 and drop into the microtiter plate 1200 positioned below. This droplet formation may help offset the capillary forces that may occur from small volume flow in the very small channels.

As can be seen in FIGS. 12a and 12b, interposer 1400 may deliver small quantities of material from the MEMS valve 1 in sort channel 1122. The material may be combined in this channel with the carrier fluid through an opening in the droplet region 1450 or sort channel 1122. Waste channel 1140 may deliver the non-target material to the waste reservoir 40 in the disposable cartridge 1000 or to a waste well 1210' in microtiter plate 1200'.

The interposer 1400 may be made from polycarbonate, polymethyl methacrylate (PMMA), or cyclic olefin polymer (COP), by injection molding, embossing, laser machining or 3D printing. The tolerances on the passages in the interposer 1400 may be about +/−1-10 microns on a total diameter of about 100 to 400 microns. The corresponding passages in the MEMS valve 1 may be about 50 to 150 microns. The MEMS valve 1 may be glued to the interposer by seating it in the chip cavity 1470 shown in FIG. 10. The cavity 1470 may be formed sufficiently precisely that the passages in MEMS valve 1 roughly overlap the passages in interposer 1400 as described above. The allowed mismatch may be up to about 20 microns, easily achievable, and adequate to prevent leaks. A pick and place machine, well known in printed circuit board manufacturing, may be adequate for this task. After alignment, the MEMS valve 1 may be glued in place within cavity 1470.

The interposer 1400 may then be glued to the cartridge base 1130 with glue or cement, by locating the interposer 1400 locating holes 1410 against corresponding posts in cartridge body 1000. Since this glue or cement will be required to be watertight, yet not interfere with passages 1120, 1122 or 1140, some features may be formed as glue dams 1460 around these channels, as shown in FIGS. 12a and 12b. These glue dams 1460 may serve to keep the liquid, uncured glue from entering the small channels 1120, 1122 and 1140. The features 1460 may be raised ridges of plastic material which prevent the liquid from entering the channels or other depressions. In particular, glue may be injected into a port that gives access to the interface between interposer 1400 and the remainder of cartridge body 1000. The glue will wick around this area but may be kept out of microfluidic passageways 1120, 1140 and 1122 by glue dams 1460 that surround these passageways as shown in FIG. 12a. The glue dams may reduce the thickness of the interface between interposer 1400 and the remainder of cartridge body 1000 from about 5 to 10 μm to 0.2 to 2 μm thereby creating a capillary effect that may prevent the glue from flowing beyond the dam into the microfluidic passageways. It should be understood that these dimensions are exemplary only, and that such details will depend on the specifics of the application. Depending on the type of glue used, the liquid glue may be cured by heat, pressure or exposure to UV radiation, for example.

FIG. 12b is a simplified perspective view of the obverse side of the interposer 1400. This side includes the seating area 1470 for MEMS valve 1. The MEMS valve 1 may be glued or otherwise bonded against the features of seating area 1470. Also shown is the output orifice of dropper region 1450.

Exemplary dimensions for the features in disposable cartridge 1000 and interposer 1400 may be as follows: interposer may be 16 mm length, 6 mm width, 1 mm height. The waste and sample reservoirs may be 20 mm in diameter. The sample channel 1120, carrier channel 1122 and waste channel 1140 may each be 300 microns in width. The height of the glue dams may be about 20-50 microns high.

Figure 13:
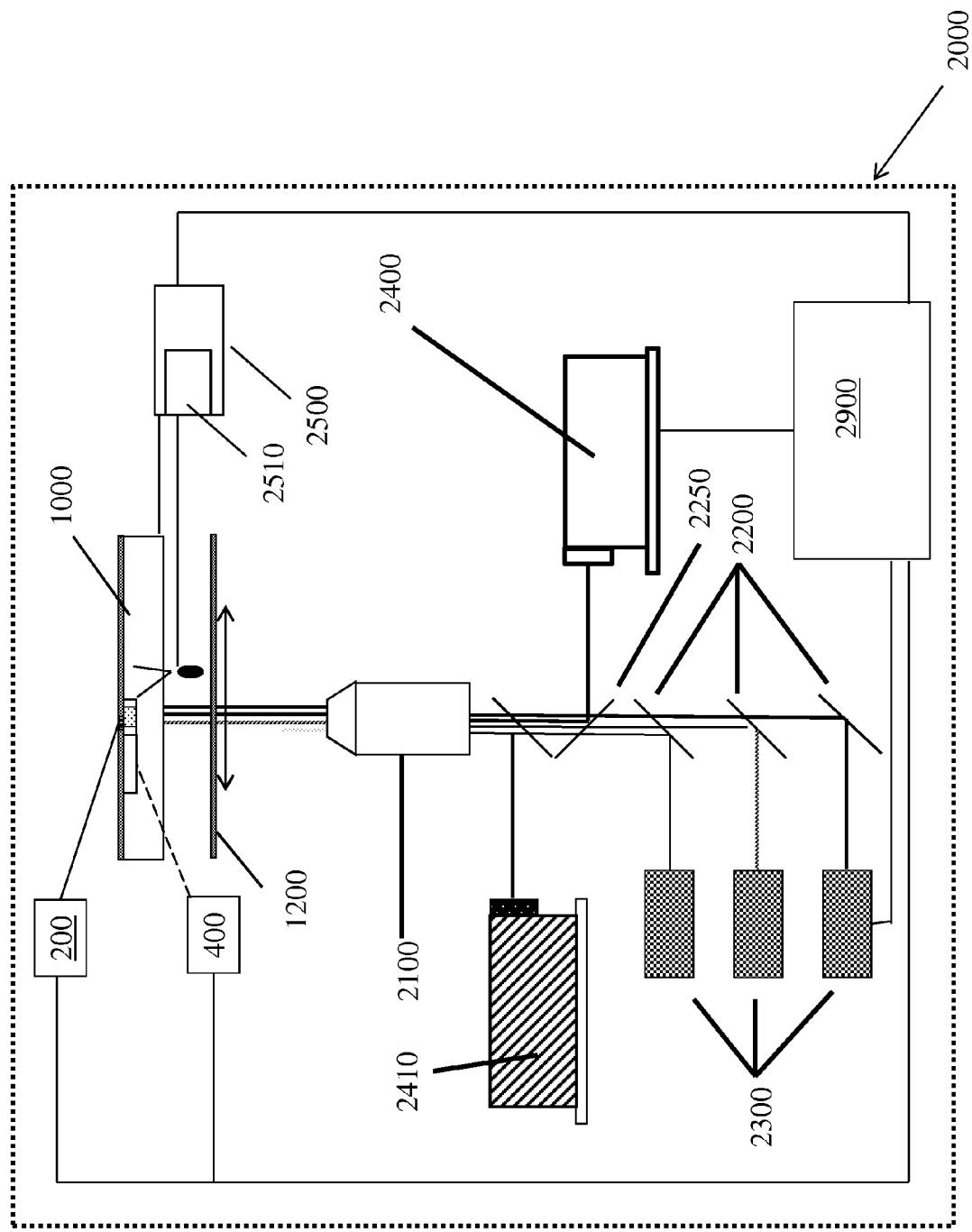
FIG. 13 is a schematic view of the MEMS single particle separation system using a MEMS particle separation device.

FIG. 13 is a schematic illustration of the MEMS-based single particle separating system 2000, which may use a MEMS-based single particle separation device 10 with an interposer 1400 housed in a disposable cartridge 1000, What follows is a description of some other components of the system and how they interact with the MEMS-based single particle separation device 10. In particular, FIG. 13 lays out the optical path of the interrogating laser for interrogation region 200, and the control of fluid flow in the system, and control of MEMS-based single particle separation device 10.

As shown in FIG. 13, the microfabricated MEMS valve 1 and interposer 1400 may be housed in the disposable cartridge 1000, described above. The disposable cartridge 1000 may be loaded onto a movable stage and oriented with respect to detection optics and interrogating lasers 2400 in the single particle separating system 2000. Fluid then flows through the MEMS valve 1 from fluid reservoirs also housed in disposable cartridge 1000 via passageways in the interposer 1400, as was described above with respect to FIGS. 10-12.

In the normal operation of system 2000, the target particle may be a particular cell, such as a stem cell, or a cancer cell, which has been tagged with a fluorescent marker. This marker emits photons having a particular energy when irradiated with a laser 2400 operating at a predefined wavelength. Accordingly, in this cell sorting system, a laser source 2400 may be directed by a turning mirror 2250 through the detection/collection optics 2100 to the laser interrogation region 200 as was shown in FIGS. 8 and 9. The optical axis of the detection/collection optics 2100 and the laser source 2400 may be collinear, at least over a portion of the optical path. Thus, the orientation of the laser application and optical detection along this optical axis may be perpendicular or orthogonal to the substrate fabrication plane, orthogonal to the plane of motion of the movable valve 110 and orthogonal to the flow of the sample fluid through the detection region.

The fluorescence emitted from the irradiated particles may be shaped by detection/collection optics 2100 and separated by dichroic minors 2200 and directed into a bank of photodetectors 2300. A plurality of photodetectors may accommodate multiple wavelengths of emitted light, for multiparametric detection. The signal output by the photodetectors 2300 indicates the presence or absence of the target particle in the laser interrogation region 200. The signal may be delivered to a controller 2900, which manages the relative timing of the components in the MEMS-based single particle separating system 2000, and collects the data. The controller 2900 may be a general purpose computer or a specialized circuit or ASIC. Upon detection of the target particle, a signal is generated by the controller 2900 which energizes the force-generating or flux-generating apparatus 400.

The controller 2900 may also provide the fluidic control to the MEMS valve 1 or X1, and carrier fluid valve X2, via one or more pneumatic, hydraulic, piston-based or mechanical force-based mechanisms which are illustrated generically by fluid control means 2500. Fluid control means 2500 may include mechanisms for opening and closing valves X1 and X2. Fluid control means, shown generically in FIG. 13 may be understood to include the droplet detecting means 2510, which detects the formation of the quantity of fluid at the end of dropper 122. The droplet detection means may detect the formation of an adequately sized droplet for blotting into a receiver such as titer plate 1200, 1200', or the release of a droplet into the receiver 1200, 1200'. The droplet detection means may detect that the droplet is ready to, or has been dispensed from, the dropper 122 and may be based on a weight, vibration, or optical measurement, for example. The rate at which droplets are detected may be monitored by the controller 2900, which may maintain the fluid control means 2500 and thus the rate of flow of carrier fluid from carrier fluid reservoir 4.

The force generating apparatus 400 is a device which causes a force to arise in the movable structure 110 itself, causing the motion of the movable structure. This force-generating apparatus 400 may not be directly mechanically coupled to the MEMS particle manipulation device 10, as indicated by the dashed line in FIG. 13. For example, the force-generating apparatus 400 may be a source of magnetic flux which causes a magnetostatic force to arise in an inlaid permeable material 116 in the MEMS movable valve 110 as described previously. Accordingly, flux generating apparatus 400 may be an electromagnet with a magnetic core and windings. This force may pull the movable valve 110 toward the force-generating apparatus 400, opening the dropper structure 122 and closing the waste channel 140, as was shown in FIGS. 8 and 9. Importantly, the force-generating apparatus 400 may reside in the MEMS-based single particle separating system 2000, rather than in the MEMS valve 1. As mentioned previously, this may reduce the cost and complexity of the MEMS valve 1, which may be housed in the disposable portion 1000 of the system 1.

Another optional laser 2410 may also be included to provide a second optical channel in cell sorting system 2000.

Upon passing through the detection region 200, a signal is generated by the detector 2300 indicating that a target particle is present in the interrogation region 200. After a known delay, a signal is generated by the controller 2900 which indicates that the sorting gate, i.e. the movable valve 110 is to be opened, in order to separate the target particle which was detected, from the other components in the fluid stream. The movable MEMS valve 110 may comprise permeable magnetic materials 116 as mentioned previously, so that the magnetic force may arise in it in the presence of a magnetic field. When the signal is generated by the controller 2900, a force arises in the embedded magnetically permeable material 116 which draws the movable valve 110 toward the force generating apparatus 400. This motion may close off waste channel 140 and redirect the target particle into a dropper structure 122. The sorted sample is subsequently collected from a sort reservoir at the end of the dropper structure 122, which holds the sorted sample. As mentioned previously, the controller 2900 may also control flow rates based on the rate at which sorting events are recorded.

Having now been separated from the fluid stream, the target particle passes into the sort channel 22, where it may be mixed with the carrier fluid from fluid carrier channel 24, as was described previously. The fluid may finally enter the tapered dropper structure 122, from which it may fall as a droplet or be blotted into microtiter plate 1200. The microtiter plate may be positioned by a robot (not shown in FIG. 13).

The fluid control means 2500 may control the direction and velocity of fluid flowing through the channels of the MEMS valve 1, including the sample fluid and the carrier fluid. For simplicity of depiction, these control lines and valving mechanisms are not shown in FIG. 13. Furthermore, FIG. 13 may omit many other signal and control lines, which are implicitly included in the MEMS-based single particle separating system 2000.

The controller 2900 may control most aspects of the MEMS-based single particle separating system 2000, including carrier valve X2, robotic means 1500, laser interrogation means 2400 and MEMS valve 1. As mentioned previously, the controller 2900 may implement the timelines shown in FIGS. 2 and 4, by opening and closing the various valves and by activating the robotic means that controls the positioning of microtiter plate 1200 or 1200'. The details as to how these control algorithms may be implemented should be clear to one of skill in the art. To maintain clarity of depiction, many of the connections and relationships may not be shown in FIG. 13, and many smaller details and features may be omitted from the figure for the sake of simplicity.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. While the systems and methods above are directed to the separation of biological materials such as cells, they may also be applied to the separation of other sorts of inert particles suspended in a fluid, such as paints or slurries. And while the systems and methods are described above with respect to separating a single, individual particle or cell, it should be understood that a plurality of cells or particles may be separated. Accordingly, the exemplary implementations set forth above, are intended to be illustrative, not limiting.

What is claimed is:

1. A particle separation device, comprising:
   a plurality of microfluidic channels, including a sample inlet channel through which a sample fluid flows, wherein the sample fluid includes one or more target particles and non-target material;
   an interrogation region disposed in the sample inlet channel, wherein the one or more target particles are distinguished from non-target material in the fluid stream;
   a microfabricated fluidic valve formed on a surface of the substrate, wherein the microfabricated fluidic valve redirects the target particles into one of a plurality of output channels, based on a signal from the interrogation region, and wherein the motion of the fluidic valve is substantially in a first plane parallel to the surface of the substrate; wherein the sample inlet channel is substantially also in the first plane parallel to the surface of the substrate, and wherein at least one of the output channels is in a second, different plane than the fluidic valve and the sample inlet channel;
   a carrier fluid inlet which supplies a carrier fluid to surround the one or more target particles with a quantity of carrier fluid; and
   an output structure that dispenses a plurality of discrete quantities of carrier fluid and the one or more target particles onto a receptacle.

2. The particle separation device of claim 1, wherein the carrier fluid inlet is disposed downstream of the microfabricated fluidic valve, and the discrete quantities of carrier fluid are dispensed as droplets, and the receptacle is a titer plate with a plurality of wells formed therein.

3. The particle separation device of claim 2, wherein the carrier fluid inlet is coupled to the sort channel and further includes a valve that controls the flow of the carrier fluid into the sort channel.

4. The particle separation device of claim 2, wherein the output structure is a dropper formed on an interposer, wherein the interposer also holds the microfabricated fluidic valve and the dropper forms liquid droplets, each of which which contains a discrete quantity of carrier fluid and the one or more target particles.

5. The particle separation device of claim 4, wherein the interposer further includes the plurality of microfluidic channels that connect the microfabricated fluidic valve to a sample reservoir, a carrier fluid reservoir, and a waste reservoir.

6. The particle separation device of claim 4, further comprising a robot that positions the titer plate with the plurality of wells, to receive the droplet.

7. The particle separation device of claim 6, wherein the titer plate is positioned by a robot, to collect each droplet in a separate well.

8. The particle separation device of claim 5, wherein the titer plate includes at least one larger waste well and a plurality of smaller, target particle wells.

9. The particle separation device of claim 4, further comprising a detector for detecting that each droplet is ready to, or has been dispensed from, the dropper.

10. The particle separation device of claim 1, wherein the carrier fluid inlet is coupled to the sample inlet channel.

11. The particle separation device of claim 5, wherein the sample reservoir and waste reservoir, interposer and microfabricated valve are contained in a disposable, removable cartridge.

12. A particle separation device, comprising:
a plurality of microfluidic channels, including a sample inlet channel and a sort channel, through which a sample fluid flows, wherein the sample fluid includes one or more target particles and non-target material;
an interrogation region disposed in the sample inlet channel, wherein the one or more target particles are distinguished from non-target material in the fluid stream;
a microfabricated fluidic valve configured to separate the one or more target particles and direct the one or more target particles into the sort channel;
a carrier fluid inlet which supplies a carrier fluid to surround the one or more target particles with a quantity of carrier fluid; and
an output structure that dispenses a plurality of discrete quantities of carrier fluid and the one or more target particles onto a receptacle;
wherein the microfabricated fluidic valve comprises:
a microfabricated, movable member formed on a substrate, and having a first diverting surface, wherein the microfabricated, movable member moves from a first position to a second position in response to a force applied to the microfabricated, movable member, wherein the motion is substantially in a first plane parallel to the surface of the substrate;
the sample inlet channel formed in the substrate and through which the sample fluid flows, the fluid including at least one target particle and non-target material, wherein the sample inlet channel is substantially parallel to the first plane to the surface of the substrate;
a plurality of output channels into which the microfabricated, movable member diverts the fluid, and wherein the at least one of the output channels is not parallel to the first plane, and wherein at least one output channel is located directly below at least a portion of the microfabricated, movable member over at least a portion of its motion.

13. The particle separation device of claim 12, wherein the plurality of output channels comprises the sort channel and a waste channel, wherein flow in the sort channel is substantially antiparallel to flow in the sample inlet channel, and wherein flow in the waste channel is substantially orthogonal to flow in the sample inlet channel and the sort channel.

14. The particle separation device of claim 12, further comprising:
a first permeable magnetic material inlaid in the movable member, the first permeable material having a relative permeability of at least about 100;
a first stationary permeable magnetic feature disposed on the substrate; and
a first source of magnetic flux external to the movable member and substrate on which the movable member is formed.

15. The particle separation device of claim 12, wherein the movable member moves from the first position to the second position when the source of magnetic flux is activated.

16. The particle separation device of claim 1, wherein the force is at least one of magnetic, electrostatic, and piezoelectric.

17. The particle separation device of claim 1, wherein the target particle comprises at least one of a stem cell, a cancer cell, a T-cell, a zygote, a component of blood, a protein, a DNA fragment, and a bacteria.

18. A particle separation system, comprising:
at least one laser source which generates laser light;
a removable, disposable cartridge that houses a particle separation device of;
the particle separation device, comprising:
a plurality of microfluidic channels, including a sample net channel through which a sample fluid flows, wherein the sample fluid includes one or more target particles and non-target material;
an interrogation region disposed in the sample inlet channel, wherein the one or more target particles are distinguished from non-target material in the fluid stream;
a microfabricated fluidic valve formed on a surface of the substrate wherein the microfabricated fluidic valve redirects the target particles into one of a plurality of output channels, based on a signal from the interrogation region, and wherein the motion of the fluidic valve is substantially in a first plane parallel to the surface of the to the surface of the substrate, and wherein at least one of the output channels is in a second, different plane than the fluidic valve and the sample inlet channel;
a carrier fluid net which supplies a carrier fluid to surround the one or more target particles with a quantity of carrier fluid; and
an output structure that dispenses a plurality of discrete quantities of carrier fluid and the one or more target particles onto a receptacle;
an optical lensing system which directs the laser light to the interrogation region;
a controller configured to detect the formation of one or more droplets on the outlet; and
an indexed receptacle for storing the one or more droplets.

* * * * *